US010312566B2

(12) United States Patent
Yamada

(10) Patent No.: US 10,312,566 B2
(45) Date of Patent: Jun. 4, 2019

(54) CABLE CONNECTION STRUCTURE AND ENDOSCOPE DEVICE

(71) Applicant: OLYMPUS CORPORATION, Tokyo (JP)

(72) Inventor: Junya Yamada, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 255 days.

(21) Appl. No.: 15/255,504

(22) Filed: Sep. 2, 2016

(65) Prior Publication Data
US 2016/0372848 A1    Dec. 22, 2016

Related U.S. Application Data

(63) Continuation of application No. PCT/JP2015/058341, filed on Mar. 19, 2015.

(30) Foreign Application Priority Data

Mar. 20, 2014   (JP) .................... 2014-059189

(51) Int. Cl.
*H01P 5/08* (2006.01)
*H05K 1/11* (2006.01)
(Continued)

(52) U.S. Cl.
CPC ............ *H01P 5/08* (2013.01); *A61B 1/00124* (2013.01); *A61B 8/12* (2013.01); *H01R 9/0515* (2013.01);
(Continued)

(58) Field of Classification Search
CPC .... A61B 1/00124; A61B 8/12; H01R 12/592; H01R 12/598; H01R 12/62; H01R 9/0515;
(Continued)

(56) References Cited

U.S. PATENT DOCUMENTS 6,857,898 B2 * 2/2005 Engquist .............. H01R 9/0515
                                                             439/493
7,520,757 B2    4/2009 Bartholomew
(Continued)

FOREIGN PATENT DOCUMENTS

CN        101502187 A    8/2009
CN        102804507 A    11/2012
(Continued)

OTHER PUBLICATIONS

International Search Report dated Jun. 9, 2015 issued in PCT/JP2015/058341.

*Primary Examiner* — Rakesh B Patel
*Assistant Examiner* — Jorge L Salazar, Jr.
(74) *Attorney, Agent, or Firm* — Scully, Scott, Murphy & Presser, P.C.

(57) ABSTRACT

A cable connection structure includes a substrate and a coaxial cable connected to the substrate. The coaxial cable has: a conductor; an inner insulator that coats an outer periphery of the conductor; a shield that coats an outer periphery of the inner insulator; and an outer insulator that coats an outer periphery of the shield. The substrate has: a plate-shaped insulating base material; a conductor connection electrode to which the conductor is connected; and a shield connection electrode to which the shield is connected. A ground is provided on a back surface of the base material opposite to where the conductor connection electrode is formed. The shield connection electrode is an exposed portion of the ground. At a connection part of the substrate to which the coaxial cable is connected, the shield connection electrode, the base material, and the conductor connection electrode are bared in a stepwise fashion.

12 Claims, 12 Drawing Sheets

(51) Int. Cl.
  *H01R 9/05*    (2006.01)
  *H01R 12/59*   (2011.01)
  *H01R 12/62*   (2011.01)
  *A61B 1/00*    (2006.01)
  *A61B 8/12*    (2006.01)
  *H05K 3/34*    (2006.01)

(52) U.S. Cl.
  CPC ......... *H01R 12/592* (2013.01); *H01R 12/598* (2013.01); *H01R 12/62* (2013.01); *H05K 1/117* (2013.01); *H01P 5/085* (2013.01); *H05K 3/3405* (2013.01); *H05K 2201/0919* (2013.01); *H05K 2201/09809* (2013.01); *H05K 2201/09845* (2013.01); *H05K 2201/10287* (2013.01); *H05K 2201/10356* (2013.01)

(58) Field of Classification Search
  CPC ........... H05K 1/117; H05K 2201/0919; H05K 2201/09809; H05K 2201/09845; H05K 2201/10287; H05K 2201/10356; H05K 3/3405; H01P 3/06; H01P 5/08; H01P 5/085

USPC ........................................ 333/236, 243, 245
  See application file for complete search history.

(56) References Cited

U.S. PATENT DOCUMENTS

| | | | |
|---|---|---|---|
| 7,658,622 | B2 | 2/2010 | Bartholomew |
| 9,356,365 | B2 | 5/2016 | Yamada et al. |
| 2004/0072468 | A1 | 4/2004 | Engquist et al. |
| 2008/0038941 | A1 | 2/2008 | Bartholomew |
| 2009/0211088 | A1 | 8/2009 | Bartholomew |
| 2013/0005181 | A1 | 1/2013 | Yamada et al. |

FOREIGN PATENT DOCUMENTS

| | | |
|---|---|---|
| JP | H08-148813 A | 6/1996 |
| JP | H09-252167 A | 9/1997 |
| JP | 2008-034207 A | 2/2008 |
| JP | 2008-210563 A | 9/2008 |
| JP | 2009-176893 A | 8/2009 |
| JP | 2011-040405 A | 2/2011 |
| JP | 2011-222277 A | 11/2011 |
| JP | 4848878 B2 | 12/2011 |

* cited by examiner

CABLE CONNECTION STRUCTURE AND ENDOSCOPE DEVICE

CROSS REFERENCES TO RELATED APPLICATIONS

This application is a continuation of PCT international application Ser. No. PCT/JP2015/058341, filed on Mar. 19, 2015 which designates the United States, incorporated herein by reference, and which claims the benefit of priority from Japanese Patent Application No. 2014-059189, filed on Mar. 20, 2014, incorporated herein by reference.

BACKGROUND

1. Technical Field

The disclosure relates to a cable connection structure in which a coaxial cable and a substrate are connected, and also relates to an endoscope device having the cable connection structure.

2. Related Art

Conventionally, an endoscope that is configured to be inserted into a cavity of a subject to perform observation or the like of a subject site has been known and widely used in a medical field or the like. The endoscope is configured such that an electronic component such as an image sensor is mounted on an electronic circuit module and the electronic circuit module is incorporated in a distal end portion of an elongated flexible insertion tool. In consideration of easiness of insertion into a patient, the distal end portion of the insertion tool is required to be thinned in diameter and shortened in length.

In response to the above-mentioned demand, a technique to lower a mounting height of a cable with respect to a substrate is known (for example, refer to JP 2009-176893 A). Specifically, in a coaxial cable connection structure that connects a cable to a substrate, a slit is formed in an end portion of the substrate, a part of the cable is dropped into the slit, and the substrate and the cable are connected, whereby the mounting height is lowered.

SUMMARY

In some embodiments, a cable connection structure includes: a substrate and a coaxial cable connected to the substrate. The coaxial cable has: a center conductor made of a conductive material; an inner insulator that coats an outer periphery of the center conductor; a shield that coats an outer periphery of the inner insulator; and an outer insulator that coats an outer periphery of the shield. The substrate has: a plate-shaped base material made of an insulator; a center conductor connection electrode to which the center conductor is connected; and a shield connection electrode to which the shield is connected. A ground is provided on a back surface of the base material opposite to where the center conductor connection electrode is formed, and the shield connection electrode is an exposed portion of the ground. A connection part of the substrate to which the coaxial cable is connected is configured such that the shield connection electrode, the base material, and the center conductor connection electrode are bared in a stepwise fashion from an end portion of the substrate to a connection surface of the substrate. An end portion of the coaxial cable is processed such that the center conductor, the inner insulator, and the shield are exposed in a stepwise fashion from a distal end portion of the coaxial cable. The processed end portion of the coaxial cable is arranged on the connection part of the substrate so that the shield and the center conductor are respectively connected to the shield connection electrode and the center conductor connection electrode bared in a stepwise fashion on the connection surface of the substrate.

In some embodiments, an endoscope device includes at least one of an ultrasound probe and an imaging device, the ultrasound probe being configured to obtain information by means of ultrasound, the imaging device being configured to obtain image information. At least one of the ultrasound probe and the imaging device has the above-described cable connection structure.

In some embodiments, a cable connection structure includes a substrate and a coaxial cable connected to the substrate. The coaxial cable has: a center conductor made of a conductive material; an inner insulator that coats an outer periphery of the center conductor; a shield that coats an outer periphery of the inner insulator; and an outer insulator that coats an outer periphery of the shield. The substrate has a first substrate and a second substrate. The first substrate has a first base material made of an insulator and a center conductor connection electrode to which the center conductor is connected such that the center conductor connection electrode is formed in the first base material so as to be flush with the first base material. The second substrate has a second base material made of an insulator and a shield connection electrode to which the shield is connected such that the shield connection electrode is formed in the second base material so as to be flush with the second base material. The first and second substrates are stacked such that the shield connection electrode and the center conductor connection electrode are bared from an end portion of the substrate toward a connection surface of the substrate. An end portion of the coaxial cable is processed such that the center conductor, the inner insulator, and the shield are exposed in a stepwise fashion from a distal end portion of the coaxial cable. The processed end portion of the coaxial cable is arranged on a connection part of the substrate so that the shield and the center conductor are respectively connected to the shield connection electrode and the center conductor connection electrode bared from the end portion of the substrate toward the connection surface of the substrate.

In some embodiments, an endoscope device includes at least one of an ultrasound probe and an imaging device, the ultrasound probe being configured to obtain information by means of ultrasound, the imaging device being configured to obtain image information. At least one of the ultrasound probe and the imaging device has the above-described cable connection structure.

The above and other features, advantages and technical and industrial significance of this invention will be better understood by reading the following detailed description of presently preferred embodiments of the invention, when considered in connection with the accompanying drawings.

DETAILED DESCRIPTION

In the following, as modes for carrying out the present invention (hereinafter referred to as "embodiment(s)"), a cable connection structure and an endoscope device will be described. The present invention is not limited by the embodiment. The same reference signs are used to designate the same elements throughout the drawings. Note that the drawings are only schematic, and a relation between thickness and width of each member and a ratio of each member or the like are different from actual ones. Dimensions and ratios in the different drawings may also be different from one another.

First Embodiment

Figure 1A:
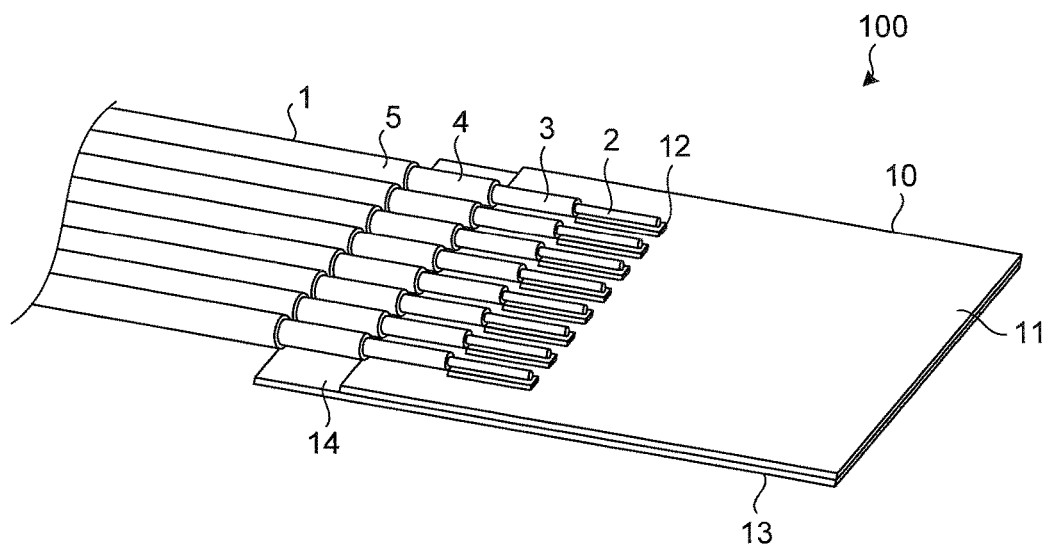
FIGS. 1A and 1B are perspective views illustrating a cable connection structure according to a first embodiment of the present invention.
Figure 1B:
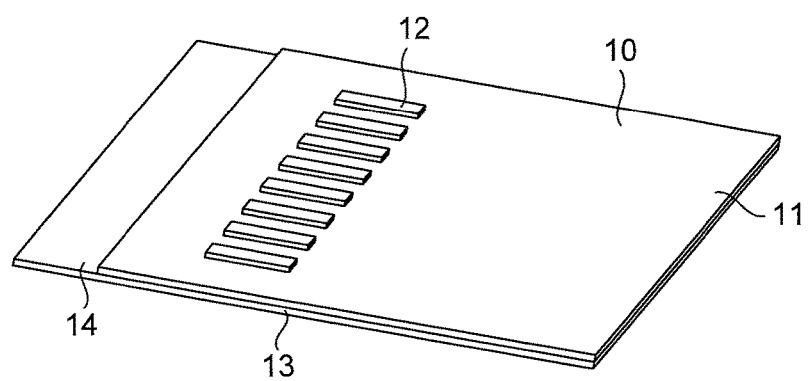
Figure 2:
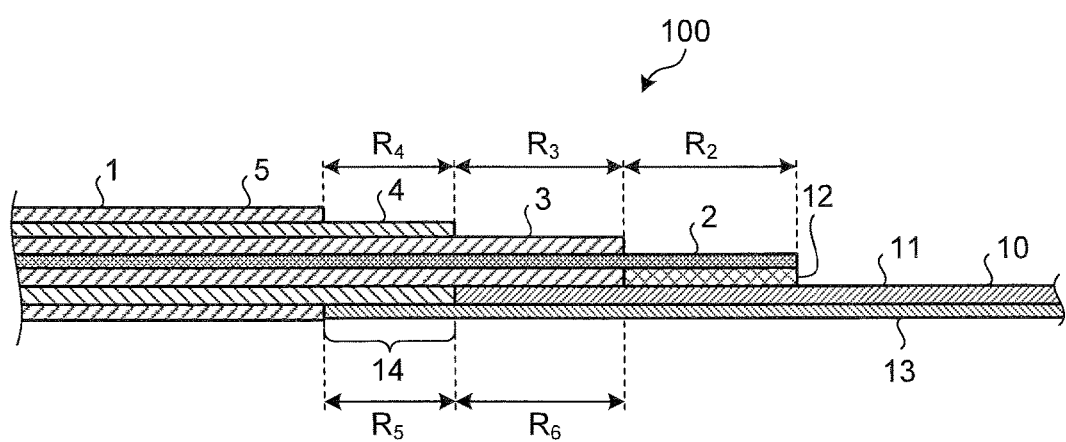
FIG. 2 is a cross-sectional view in a cable axial direction of the cable connection structure illustrated in FIGS. 1A and 1B.

FIG. 1A is a perspective view illustrating a cable connection structure according to a first embodiment of the present invention, and FIG. 1B is a perspective view of a substrate before a coaxial cable is connected to the substrate. FIG. 2 is a cross-sectional view in a cable axial direction of the cable connection structure illustrated in FIGS. 1A and 1B. As illustrated in FIGS. 1A and 1B, a cable connection structure 100 includes a plurality of coaxial cables 1 and a substrate 10 to which the coaxial cables 1 are connected. The substrate 10 may be a flexible printed substrate or a rigid substrate such as a glass epoxy substrate. A material for the substrate 10 is not limited. The cable connection structure 100 according to the first embodiment is configured such that eight coaxial cables 1 are connected to the substrate 10. However, the number of coaxial cables 1 connected to the substrate 10 may be one, and the number is not limited.

The coaxial cable 1 includes a center conductor 2, an inner insulator 3, a shield 4, and an outer insulator 5. The center conductor 2 is made of a conductive material. The inner insulator 3 coats an outer periphery of the center conductor 2. The shield 4 coats an outer periphery of the inner insulator 3. The outer insulator 5 coats an outer periphery of the shield 4. An end portion of the coaxial cable 1 that is connected to the substrate 10 is processed such that the center conductor 2, the inner insulator 3, and the shield 4 are exposed in a stepwise fashion from a distal end portion.

The substrate 10 to which the coaxial cable 1 is connected has a plate-shaped base material 11, a center conductor connection electrode 12, and a shield connection electrode 14. The base material 11 is made of an insulator. The center conductor 2 is connected to the center conductor connection electrode 12. The shield 4 is connected to the shield connection electrode 14. A ground 13 is formed on a back surface of the base material 11 opposite to where the center conductor connection electrode 12 is formed. A part of the ground 13 is bared on a surface of the substrate 10 to which the coaxial cable 1 is connected to form the shield connection electrode 14. In the first embodiment, the ground 13 is arranged on the back surface of the base material 11 opposite to where the center conductor connection electrode 12 and a signal line to which an electronic component (not illustrated) or the like is connected are formed. With this structure, a microstrip line structure can be easily achieved.

The center conductor connection electrode 12 is independently formed so that the number of center conductor connection electrodes 12 corresponds to the number of coaxial cables 1 connected on the base material 11. The center conductor 2 of the coaxial cable 1 is individually connected to each center conductor connection electrode 12. The shield connection electrode 14 is formed to extend to an end portion of the substrate 10. A plurality of shields 4 is collectively connected to the single shield connection electrode 14.

In the cable connection structure 100 of the first embodiment, a connection part of the substrate 10 to which the coaxial cable 1 is connected (left side of the substrate 10 in FIGS. 1A and 1B) is configured such that the shield connection electrode 14, the base material 11, and the center conductor connection electrode 12 are bared in a stepwise fashion from the end portion of the substrate 10 to a connection surface side of the coaxial cable 1, that is, an upper surface side. The shield connection electrode 14 may be formed in such a manner that the base material 11 is stacked on the ground 13 and then a part of the base material 11 is removed. Alternatively, a part of the ground 13 may be bared as the shield connection electrode 14 in such a manner that the base material 11 smaller than the ground 13 is stacked on the ground 13.

The center conductor connection electrode 12 preferably has a thickness nearly equivalent to a thickness of the inner insulator 3, whereby deformation of the center conductor 2 can be prevented when the coaxial cable 1 is connected to the substrate 10. The thickness of the center conductor connection electrode 12 can be adjusted by etching on a thick electrode or plating on a thin electrode. When the thickness of the center conductor connection electrode 12 is nearly equivalent to the thickness of the inner insulator 3, a deformed portion does not need to be provided on the exposed center conductor 2, whereby a strip length $R_2$ of the center conductor 2 can be shortened.

The base material 11 preferably has a thickness nearly equivalent to a thickness of the shield 4, whereby deformation of the center conductor 2 can be prevented when the coaxial cable 1 is connected to the substrate 10. The inner insulator 3 preferably has a strip length $R_3$ nearly equivalent to a length $R_6$ of the base material 11 from a connection end portion of the substrate 10 to a side of the center conductor connection electrode 12 close to the end portion of the substrate 10. The shield 4 preferably has a strip length $R_4$ nearly equivalent to a length $R_5$ of the shield connection electrode 14.

The center conductor 2 and the shield 4 of the coaxial cable 1 are electrically or mechanically connected to the center conductor connection electrode 12 and the shield connection electrode 14, respectively, using conductive bond members (not illustrated) such as, for example, solder, an anisotropic conductive film (ACF), and an anisotropic conductive paste (ACP).

In the first embodiment, the coaxial cable 1 processed such that the center conductor 2, the inner insulator 3, and the shield 4 are exposed in a stepwise fashion is arranged on the substrate 10 formed such that the shield connection electrode 14, the base material 11, and the center conductor connection electrode 12 are bared in a stepwise fashion from a side close to the end portion of the substrate 10 to the connection surface side, and the shield connection electrode 14 and the center conductor 2 are respectively connected to the shield 4 and the center conductor connection electrode 12. As a result, a height of the cable connection structure 100 can be reduced, and deformation or the like of the coaxial cable 1 at the connection portion can be prevented. Since the cable connection structure 100 according to the first embodiment is configured such that the shield 4 and the shield connection electrode 14 are directly connected, noise can be reduced. Since an end portion of the connection part of the substrate 10 connected to the coaxial cable 1 is the shield connection electrode 14, a margin between an end of the substrate and the electrodes does not need to be provided, thus the small-sized cable connection structure 100 can be achieved.

Figure 3A:
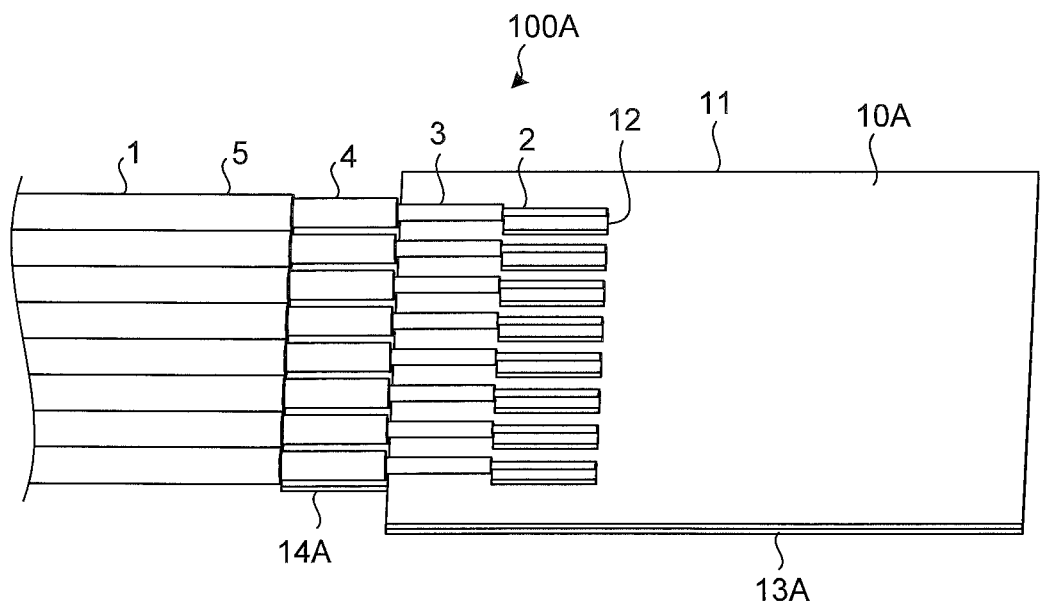
FIGS. 3A and 3B are perspective views illustrating a cable connection structure according to a first modification of the first embodiment of the present invention.
Figure 3B:
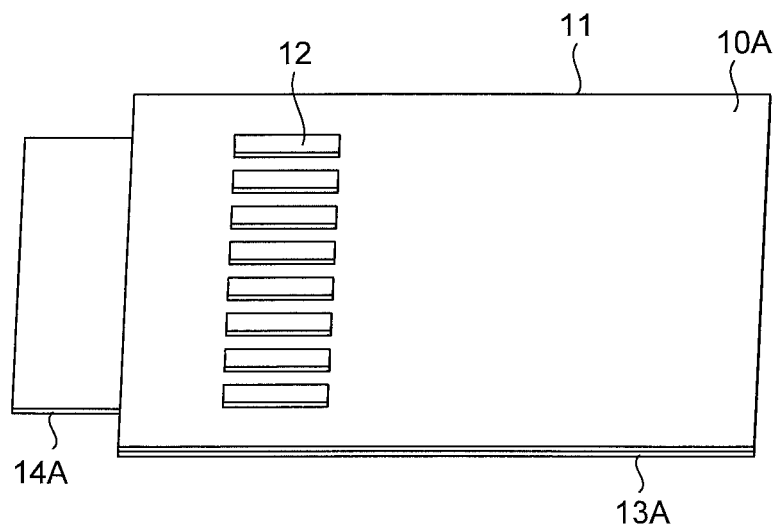

The shield connection electrode extending from the end portion of the substrate may be cut so that a length in a width direction of the shield connection electrode is shorter than a length in a width direction of the substrate. FIG. 3A is a perspective view illustrating a cable connection structure according to a first modification of the first embodiment of the present invention, and FIG. 3B is a perspective view of a substrate before a coaxial cable is connected to the substrate. As illustrated in FIGS. 3A and 3B, in a cable connection structure 100A according to the first modification, a shield connection electrode 14A extending from an end portion of a substrate 10A to which the coaxial cable 1 is connected is configured such that parts of the shield connection electrode 14A other than the connection to the coaxial cable 1, that is, both ends in a width direction of the shield connection electrode 14A, are cut off.

Since the shield connection electrode 14A is formed in such a manner that a ground 13A that is a conductive foil having a thickness of about 9 to 35 is bared, the shield connection electrode 14A does not have sufficient strength. When a stress is applied, therefore, a tear might occur. In the first modification of the first embodiment, an unnecessary part of the shield connection electrode 14A is cut off in advance, whereby a tear or the like in the shield connection electrode 14A can be prevented. In the first modification as well, the shield connection electrode 14A, the base material 11, and the center conductor connection electrode 12 are formed to be bared in a stepwise fashion from a side close to the end portion of the substrate 10A to a connection surface side, the coaxial cable 1 processed such that the center conductor 2, the inner insulator 3, and the shield 4 are exposed in a stepwise fashion is arranged on the substrate 10A, and the shield connection electrode 14A and the center conductor 2 are respectively connected to the shield 4 and the center conductor connection electrode 12. As a result, effects similar to those of the first embodiment can be obtained. In other words, a height of the cable connection structure 100A can be reduced, and deformation or the like of the coaxial cable 1 at the connection portion can be prevented.

Figure 4A:
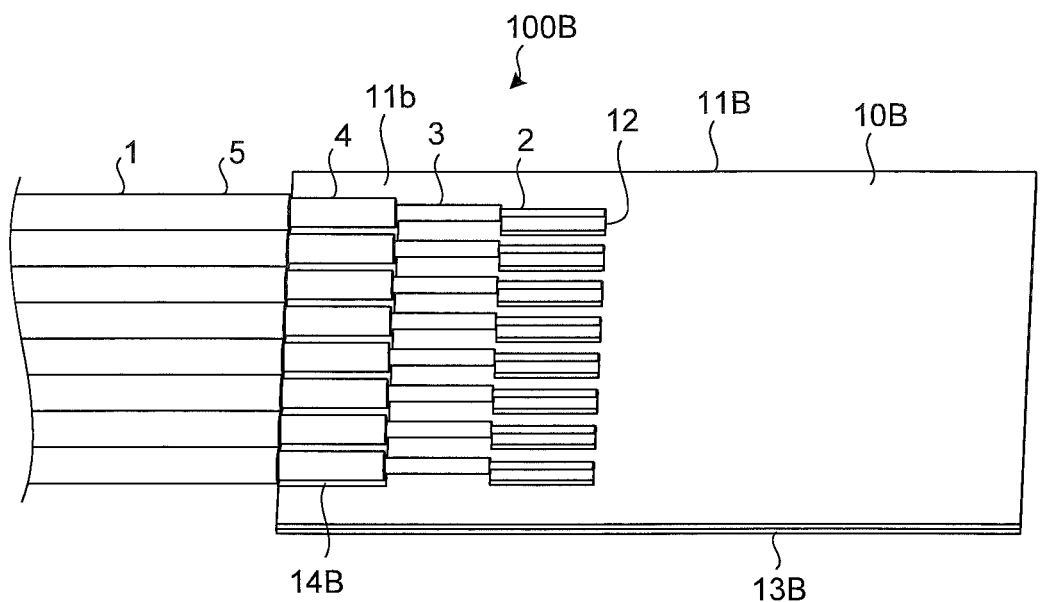
FIGS. 4A and 4B are perspective views illustrating a cable connection structure according to a second modification of the first embodiment of the present invention.
Figure 4B:
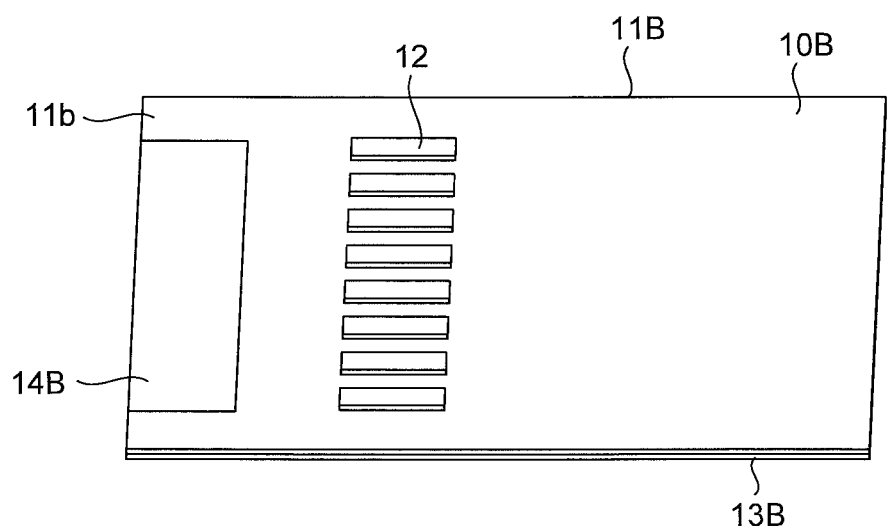

The shield connection electrode extending from the end portion of the substrate may be configured such that parts of the shield connection electrode other than a connection area between the shield connection electrode and the shield of the coaxial cable are coated with the base material. FIG. 4A is a perspective view illustrating a cable connection structure according to a second modification of the first embodiment of the present invention, and FIG. 4B is a perspective view of a substrate before a coaxial cable is connected to the substrate. A part of a ground 13B is bared to form a shield connection electrode 14B. As illustrated in FIGS. 4A and 4B, in a cable connection structure 100B according to the second modification, the shield connection electrode 14B extending from an end portion of a substrate 10B to which the coaxial cable 1 is connected may be configured such that parts of the shield connection electrode 14B other than the connection to the coaxial cable 1, that is, both ends in a width direction of the shield connection electrode 14B, are coated with a base material 11B to form a coated portion 11b.

In the second modification of the first embodiment, parts of the shield connection electrode 14B, which are not necessary for the connection, are covered with the base material 11B to form the coated portion 11b. With this structure, a tear or the like in the shield connection electrode 14B can be prevented. In the second modification as well, the shield connection electrode 14B, the base material 11B, and the center conductor connection electrode 12 are formed to be bared in a stepwise fashion from a side close to the end portion of the substrate 10B to a connection surface side, the coaxial cable 1 processed such that the center conductor 2, the inner insulator 3, and the shield 4 are exposed in a stepwise fashion is arranged on the substrate 10B, and the shield connection electrode 14B and the center conductor 2 are respectively connected to the shield 4 and the center conductor connection electrode 12. As a result, effects similar to those of the first embodiment can be obtained. In other words, a height of the cable connection structure 100B can be reduced, and deformation or the like of the coaxial cable 1 at the connection portion can be prevented.

Figure 5:
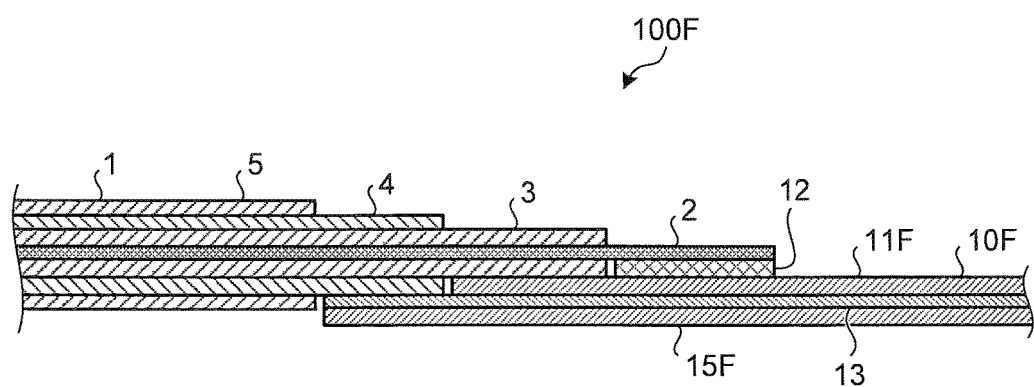
FIG. 5 is a cross-sectional view illustrating a cable connection structure according to a third modification of the first embodiment of the present invention.

Furthermore, on a back surface of the ground which is opposite to where the base material is connected, a second base material can be provided. FIG. 5 is a cross-sectional view illustrating a cable connection structure according to a third modification of the first embodiment of the present invention. In a cable connection structure 100F according to the third modification of the first embodiment of the present invention, the coaxial cable 1 is connected to a substrate 10F, and a first base material 11F on which the center conductor connection electrode 12 is formed and a second base material 15F are provided respectively on both surfaces of the ground 13 of the substrate 10F. The coaxial cable 1 is processed such that the center conductor 2, the inner insulator 3, and the shield 4 are exposed in a stepwise fashion from the distal end portion. The center conductor 2 is connected to the center conductor connection electrode 12, and the shield 4 is connected to the shield connection electrode 14.

In the third modification of the first embodiment, the second base material 15F is provided on an opposite surface of the surface of the ground 13 connected to the first base material 11F, whereby a tear or the like in the ground 13 can be prevented, and connecting workability can be improved.

Second Embodiment

Figure 6A:
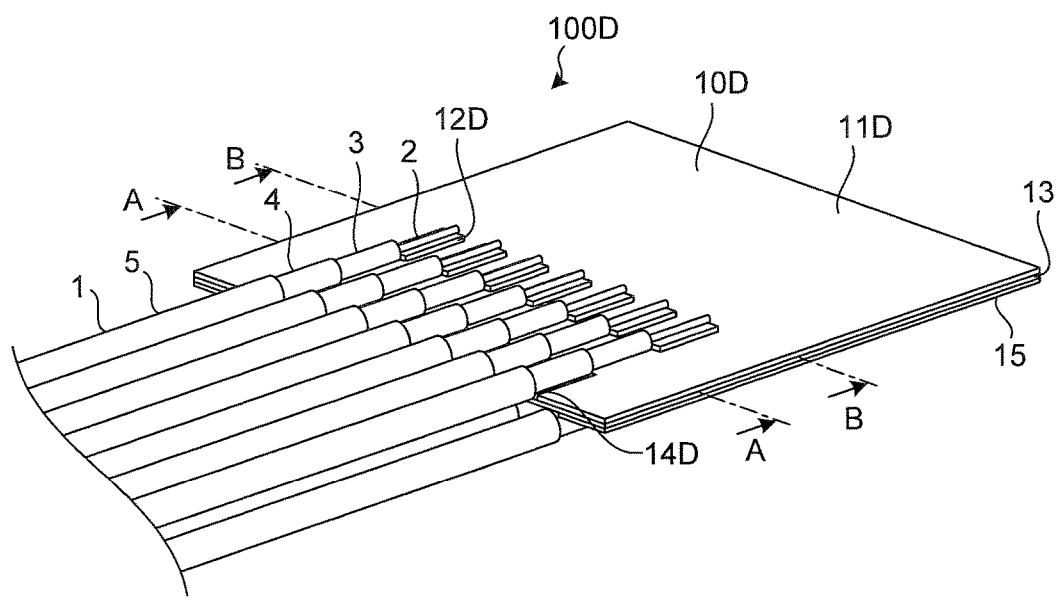
FIGS. 6A and 6B are perspective views illustrating a cable connection structure according to a second embodiment of the present invention.
Figure 6B:
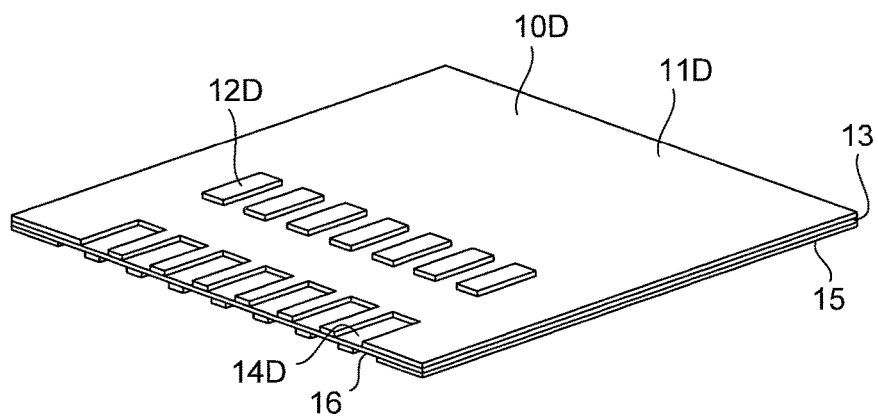
Figure 7A:
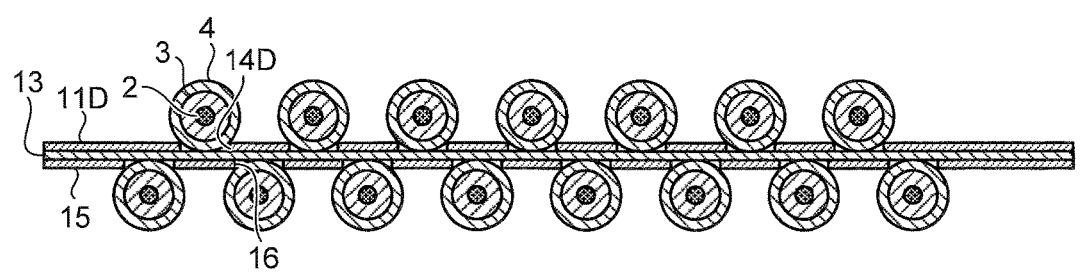
FIGS. 7A and 7B are cross-sectional views at a connection surface of a coaxial cable in the cable connection structure illustrated in FIGS. 6A and 6B.
Figure 7B:
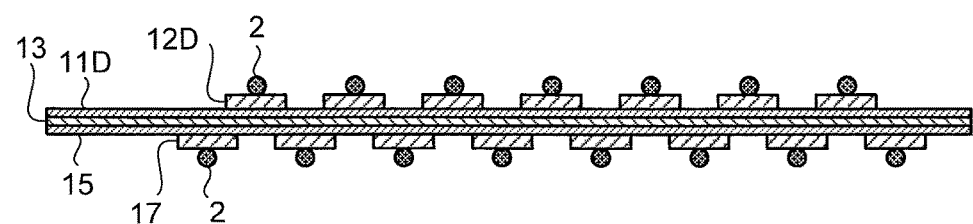

In a cable connection structure according to a second embodiment, base materials are respectively provided on both surfaces of a ground, and a coaxial cable is connected to each base material layer. FIG. 6A is a perspective view illustrating the cable connection structure according to the second embodiment of the present invention, and FIG. 6B is a perspective view of a substrate before a coaxial cable is connected to the substrate. FIG. 7A is a cross-sectional view taken along line A-A of the cable connection structure illustrated in FIGS. 6A and 6B, and FIG. 7B is a cross-sectional view taken along line B-B of the cable connection structure illustrated in FIGS. 6A and 6B.

In a cable connection structure 100D according to the second embodiment, a substrate 10D has the ground 13, and a first base material 11D and a second base material 15 are respectively provided on both surfaces of the ground 13. The first base material 11D has thereon a first center conductor connection electrode 12D. The second base material 15 has thereon a second center conductor connection electrode 17.

On the first base material 11D, the first center conductor connection electrode 12D is independently formed so that the number of first center conductor connection electrodes 12D corresponds to the number of coaxial cables 1 to be connected, and a first shield connection electrode 14D is formed so that the number of first shield connection electrodes 14D corresponds to the number of coaxial cables 1 to be connected. The first shield connection electrode 14D is formed in such a manner that a part of the first base material 11D is processed to be removed so that a part of the ground 13 is exposed. At a connection part on the first base material 11D to which the coaxial cable 1 is connected, the first shield connection electrode 14D, the first base material 11D, and the first center conductor connection electrode 12D are bared in a stepwise fashion from an end portion of the substrate 10D. The coaxial cable 1 having the end portion processed in a stepwise fashion is arranged on the connection part. Consequently, the shield 4 and the center conductor 2 are respectively connected to the first shield connection electrode 14D and the first center conductor connection electrode 12D bared in a stepwise fashion to a connection surface side.

On the second base material 15, the second center conductor connection electrode 17 is independently formed so that the number of second center conductor connection electrodes 17 corresponds to the number of coaxial cables 1 to be connected, and a second shield connection electrode 16 is formed so that the number of second shield connection electrodes 16 corresponds to the number of coaxial cables 1 to be connected. The second shield connection electrode 16 is formed in such a manner that a part of the second base material 15 is processed to be removed so that a part of the ground 13 is exposed. At a connection part on the second base material 15 to which the coaxial cable 1 is connected, the second shield connection electrode 16, the second base material 15, and the second center conductor connection electrode 17 are bared in a stepwise fashion from the end portion of the substrate 10D. The coaxial cable 1 having the end portion processed in a stepwise fashion is arranged on the connection part. Consequently, the shield 4 and the center conductor 2 are respectively connected to the second shield connection electrode 16 and the second center conductor connection electrode 17 bared in a stepwise fashion to the connection surface side.

Since the coaxial cables 1 are connected on the first base material 11D and the second base material 15, the coaxial cables 1 are connected to both surfaces of the substrate 10D. As illustrated in FIG. 7B, the first center conductor connection electrode 12D and the second center conductor connection electrode 17 are preferably arranged such that their center positions do not overlap in a width direction of the substrate 10D. Similarly, the first shield connection electrode 14D and the second shield connection electrode 16 are preferably arranged such that their center positions do not overlap in the width direction of the substrate 10D. Each electrode is arranged as described above, whereby the coaxial cables 1 can be connected to both surfaces of the substrate 10D in a houndstooth pattern. If the cables connected to both surfaces of the substrate 10D are not displaced in the width direction and the ground 13 is made of a thin conductor, the outer insulators 5 of the coaxial cables 1 interfere with one another. When the coaxial cables 1 are arranged in a houndstooth pattern, the outer insulators 5 do not interfere one another. Therefore, a height of the cable connection structure 100D can be reduced when the coaxial cables 1 are connected to both surfaces of the substrate 10D.

In the second embodiment, the first shield connection electrode 14D and the second shield connection electrode 16 are individually formed so that the number of first shield connection electrodes 14D and the number of second shield connection electrodes 16 each correspond to the number of coaxial cables 1 to be connected. However, a single first shield connection electrode and a single second shield connection electrode to which the shields 4 of the plurality of coaxial cables 1 are collectively connected may be employed.

The ground 13 as an inner layer may be two layers, whereby a conductor four-layer substrate may be employed. In this case, the first shield connection electrode 14D and the second shield connection electrode 16 are layers of the different grounds 13.

Figure 8A:
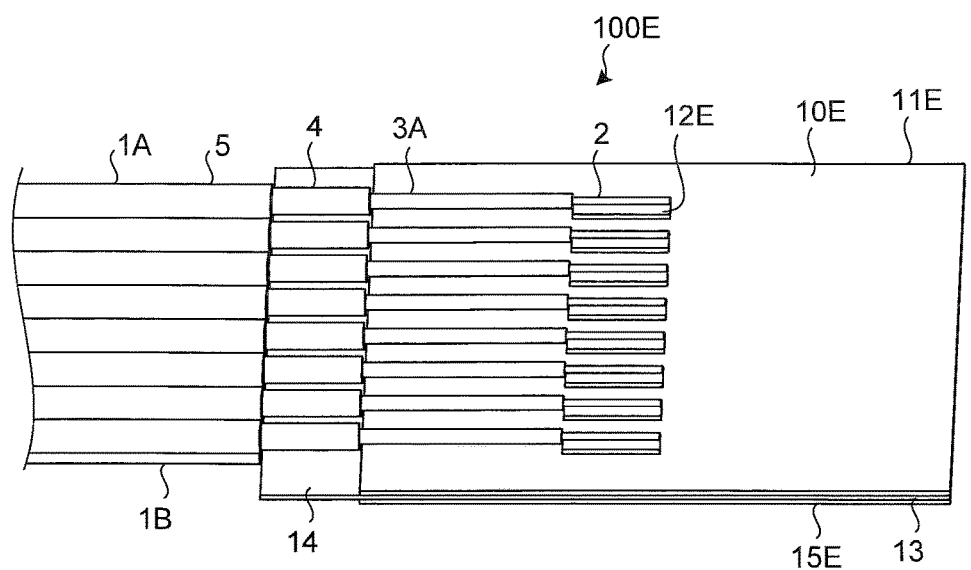
FIGS. 8A and 8B are perspective views illustrating a cable connection structure according to a modification of the second embodiment of the present invention.
Figure 8B:
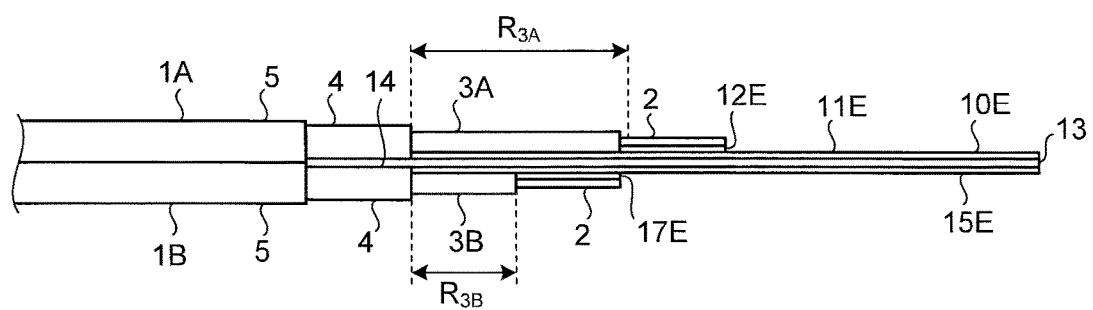

The first center conductor connection electrode and the second center conductor connection electrode may be arranged such that their center positions do not overlap in a length direction of the substrate. FIG. 8A is a perspective view illustrating a cable connection structure 100E according to a modification of the second embodiment of the present invention, and FIG. 8B is a side view of the cable connection structure 100E according to the modification of the second embodiment of the present invention.

In the modification of the second embodiment, a first center conductor connection electrode 12E is formed on a first base material 11E, and a second center conductor connection electrode 17E is formed on a second base material 15E. The first center conductor connection electrode 12E is located away from a connection end portion of a substrate 10E such that a center position of the first center conductor connection electrode 12E does not overlap a center position of the second center conductor connection electrode 17E in a length direction (axial direction of coaxial cables 1A and 1B to be connected).

Correspondingly, the coaxial cable 1A to be connected on the first base material 11E is stripped so that an exposure length ($R_{3A}$) of an inner insulator 3A of the coaxial cable 1A is longer than an exposure length ($R_{3B}$) of an inner insulator 3B of the coaxial cable 1B to be connected on the second base material 15E.

As long as the first center conductor connection electrode 12E is arranged at a position where the center position of the first center conductor connection electrode 12E does not overlap the center position of the second center conductor connection electrode 17E in the length direction (axial direction of the coaxial cables 1A and 1B to be connected), the center position of the first center conductor connection electrode 12E may overlap the center position of the second center conductor connection electrode 17E in a width direction of the substrate 10E, or alternatively, the center position of the first center conductor connection electrode 12E may be arranged so as not to overlap the center position of the second center conductor connection electrode 17E even in the width direction of the substrate 10E.

Third Embodiment

Figure 9A:
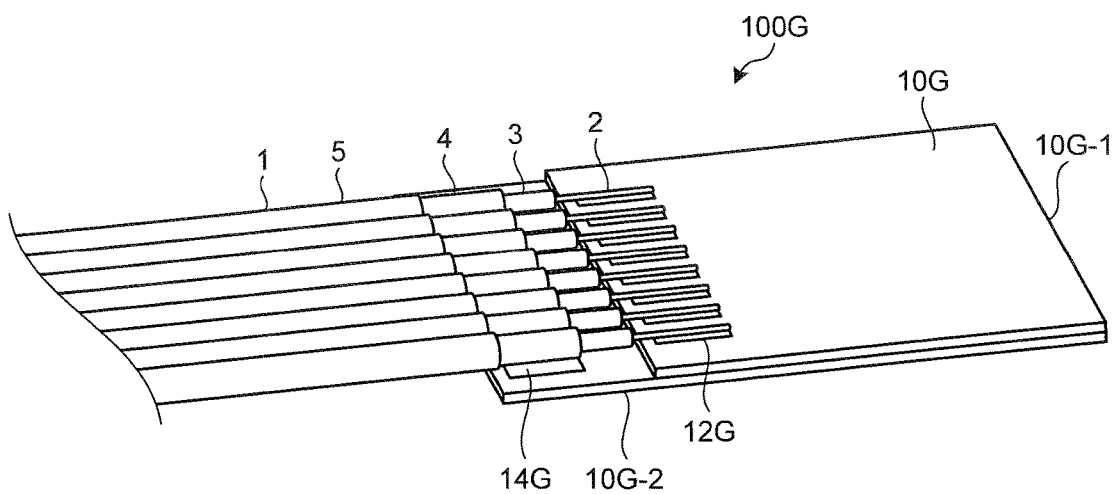
FIGS. 9A and 9B are perspective views illustrating a cable connection structure according to a third embodiment of the present invention.
Figure 9B:
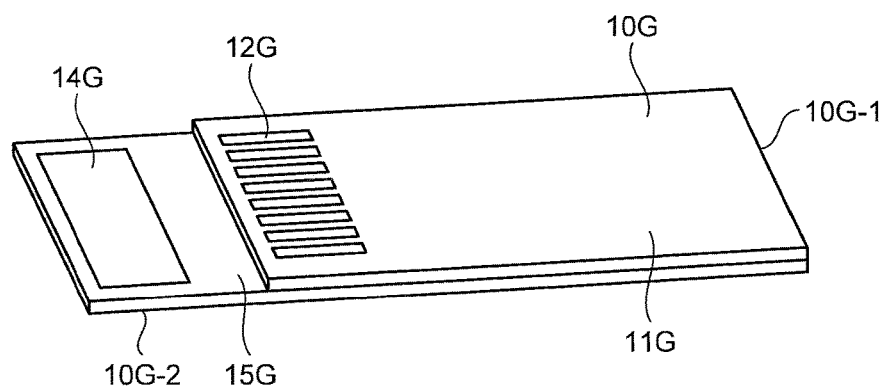
Figure 10:
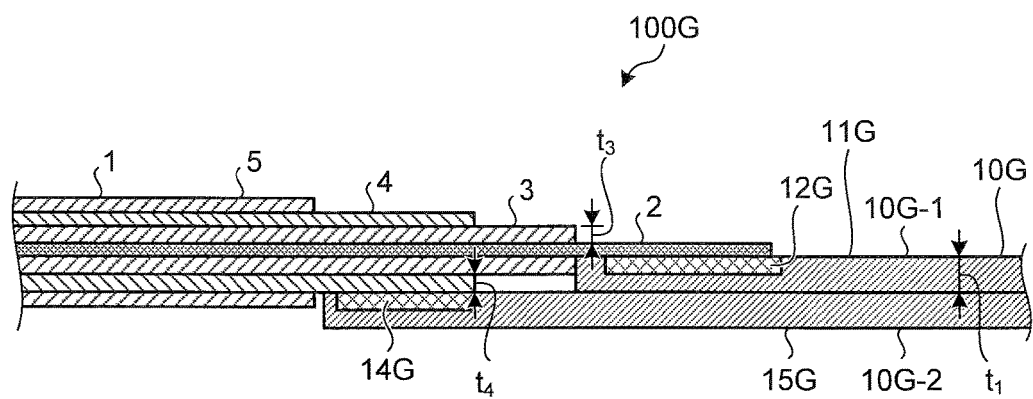
FIG. 10 is a cross-sectional view in a cable axial direction of the cable connection structure illustrated in FIGS. 9A and 9B.

In a cable connection structure according to a third embodiment, first and second substrates are stacked to form a substrate. The first substrate has thereon a center conductor connection electrode. The second substrate has thereon a shield connection electrode. FIG. 9A is a perspective view illustrating a cable connection structure 100G according to the third embodiment of the present invention, and FIG. 9B is a perspective view of a substrate before a coaxial cable is connected to the substrate. FIG. 10 is a cross-sectional view in a cable axial direction of the cable connection structure 100G illustrated in FIGS. 9A and 9B.

A substrate 10G has a first substrate 10G-1 and a plate-shaped second substrate 10G-2. The first substrate 10G-1 has thereon a center conductor connection electrode 12G to which the center conductor 2 is connected. The center conductor connection electrode 12G is formed so as to be flush with a first base material 11G made of an insulator. The second substrate 10G-2 has thereon a shield connection electrode 14G to which the shield 4 is connected. The shield connection electrode 14G is formed so as to be flush with a second base material 15G made of an insulator. The first substrate 10G-1 and the second substrate 10G-2 are stacked such that the shield connection electrode 14G and the center conductor connection electrode 12G are bared from a substrate end portion side toward a connection surface side.

The substrate 10G is a ceramic substrate and capable of improving strength while maintaining mounting density. The substrate 10G can be manufactured in the following way. Ceramic powder and a binder which are raw materials for the first base material 11G and the second base material 15G are mixed to form slurry. Then, a tape-shaped ceramic raw sheet is obtained, a conductive paste is screen-printed, and a wiring pattern and a via are formed, whereby the first substrate 10G-1 and the second substrate 10G-2 before sintering are produced. After that, the first substrate 10G-1 and the second substrate 10G-2 before sintering are stacked such that the shield connection electrode 14G and the center conductor connection electrode 12G are bared from the substrate end portion side toward the connection surface side. Heat and pressure are then applied, whereby the substrate 10G can be obtained. Since the substrate 10G is manufactured by the sintering, the center conductor connection electrode 12G and the shield connection electrode 14G are formed to be flush with the first base material 11G and the second base material 15G, respectively.

The sum of a thickness t3 of the inner insulator 3 of the coaxial cable 1 and a thickness t4 of the shield 4 is preferably substantially equal to a thickness t1 of the first base material 11G. With this structure, deformation of the center conductor 2 can be prevented when the coaxial cable 1 is connected to the substrate 10G. An outer periphery of the exposed inner insulator 3 is arranged above the second substrate 10G-2 so as not to come into contact with the second base material 15G. An end portion of the inner insulator 3 is caused to abut on an end portion of the first substrate 10G-1 to perform positioning of the coaxial cable 1 in a longitudinal direction. In a case where the positioning of the coaxial cable 1 in the longitudinal direction does not need to be strictly performed, the end portion of the inner insulator 3 may not abut on the end portion of the first substrate 10G-1.

Figure 11:
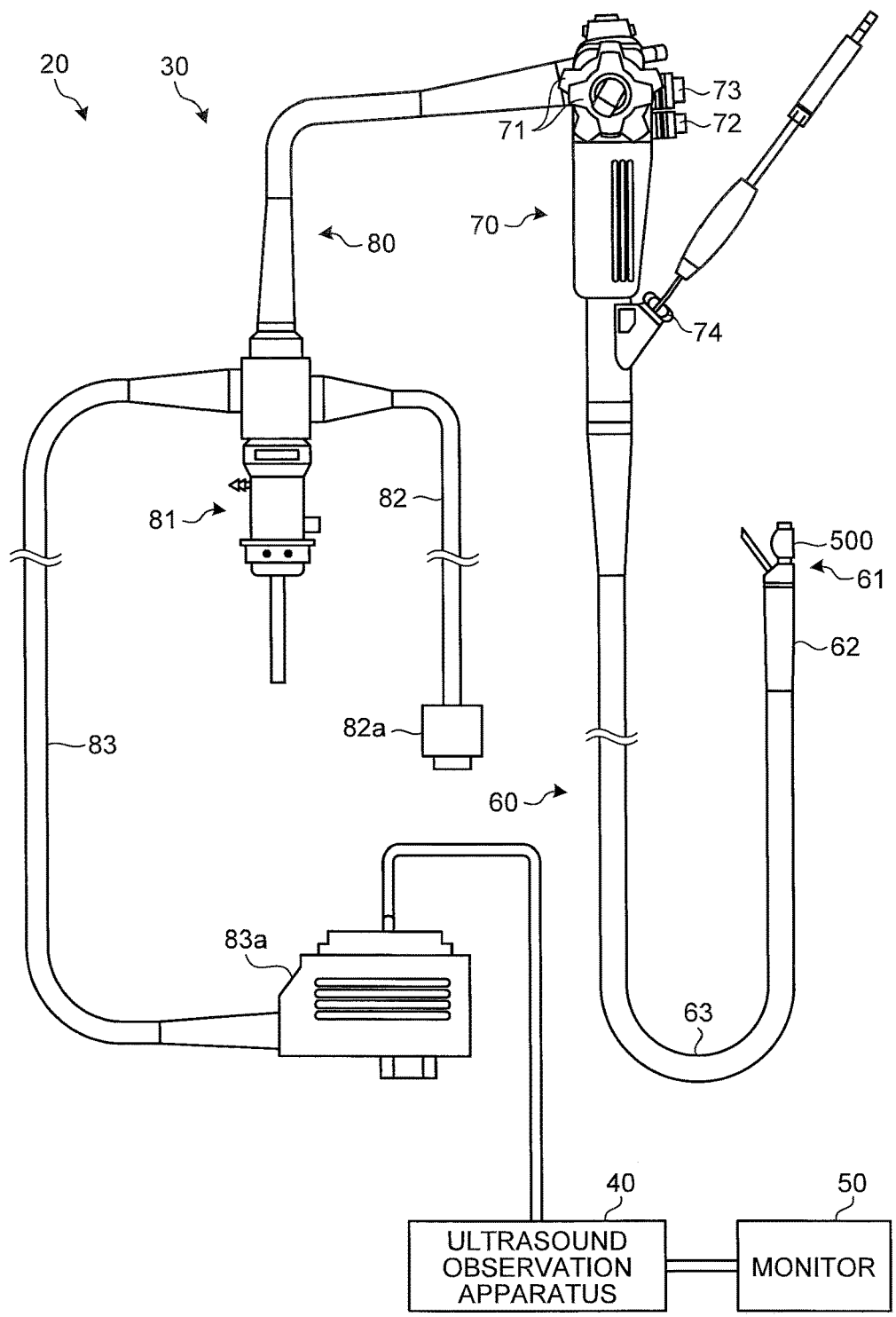
FIG. 11 is an overall configuration diagram of an ultrasound endoscope system using an ultrasound probe.
Figure 12:
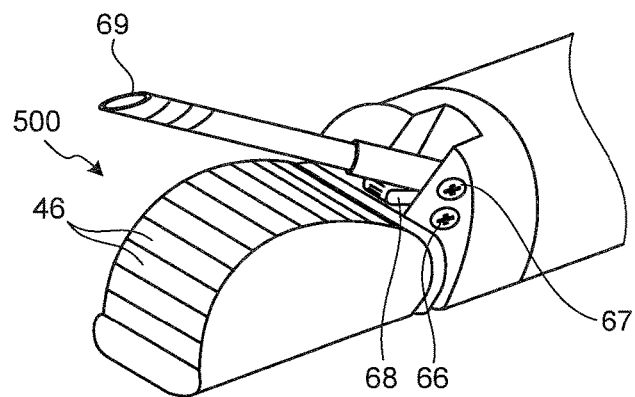
FIG. 12 is a schematic view illustrating a structure of a distal end portion of an insertion portion of the ultrasound endoscope system in FIG. 11.
Figure 13:
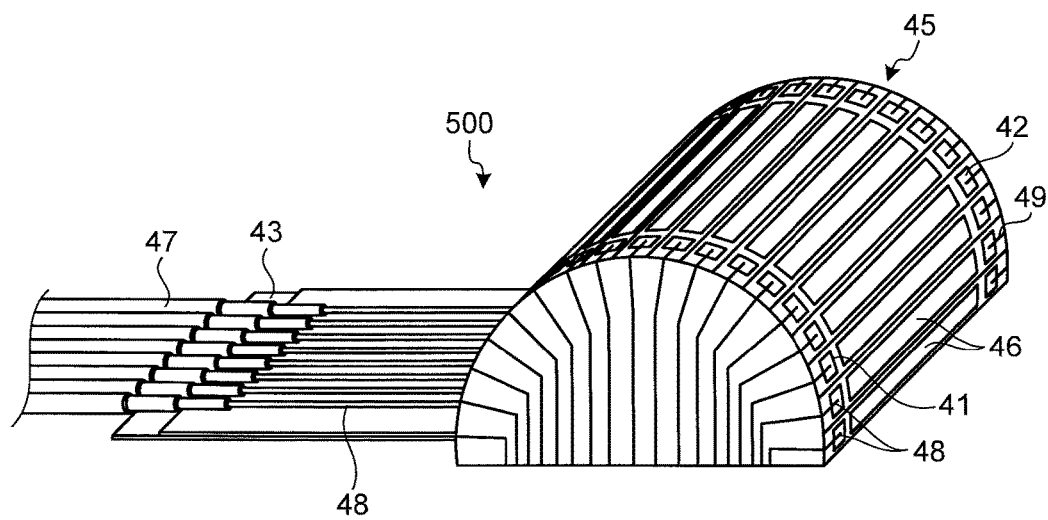
FIG. 13 is a schematic view illustrating a structure of the ultrasound probe at the distal end portion in FIG. 12.

The cable connection structures according to the above-mentioned first to third embodiments can be suitably applied to an ultrasound module having a plurality of ultrasound transducers. FIG. 11 is an overall configuration diagram of an ultrasound endoscope system including an ultrasound probe. FIG. 12 is a schematic view illustrating a structure of a distal end portion of an insertion portion of the ultrasound endoscope system in FIG. 11. FIG. 13 is a schematic view illustrating a structure of the ultrasound probe at the distal end portion in FIG. 12.

First, an overall configuration of an ultrasound endoscope system 20 will be described. The ultrasound endoscope system 20 illustrated in FIG. 11 includes an ultrasound endoscope 30, an ultrasound observation apparatus 40, and a monitor 50. The ultrasound endoscope 30 includes an elongated insertion portion 60, an operating unit 70, and a universal code 80. The insertion portion 60 is inserted into a body. The operating unit 70 is continuously provided at a proximal end of the insertion portion 60. The universal code 80 extends from a side portion of the operating unit 70.

At a proximal end portion of the universal code 80, a connector 81 connected to a light source device (not illustrated) is arranged. A cable 82 and a cable 83 extend from the connector 81. The cable 82 is coupled to a camera control unit (not illustrated) via a connector 82a. The cable 83 is detachably coupled to the ultrasound observation apparatus 40 via a connector 83a. The ultrasound observation apparatus 40 is coupled to the ultrasound endoscope 30 via the connector 83a, and the monitor 50 is coupled to the ultrasound endoscope 30 via the ultrasound observation apparatus 40.

A principle part of the insertion portion 60 includes a distal end rigid portion (hereinafter referred to as a "distal end portion") 61, a bending portion 62, and a flexible tube portion 63, continuously provided in order from a distal end side. The bending portion 62 is located at a rear end of the distal end portion 61. The flexible tube portion 63 has a thin diameter, a long length, and flexibility. The flexible tube portion 63 is located at a rear end of the bending portion 62 and extends to the operating unit 70.

As illustrated in FIG. 12, an ultrasound probe 500 is arranged on a distal end side of the distal end portion 61. On a proximal side beyond the ultrasound probe 500, at the distal end portion 61, an illumination lens 66 constituting an illumination optical system, an observation lens 67 of an observation optical system, and a forceps port (not illustrated) are arranged. The forceps port, a distal end opening, is a guide port of a treatment tool insertion passage that is also used as a suction port. A treatment tool raising base 68 is arranged at the forceps port. An operation wire (not illustrated) is connected to the treatment tool raising base. When a forceps raising knob (not illustrated) is operated, the operation wire is pulled, whereby a guide angle of a puncture needle 69 guided out of the treatment tool insertion passage can be adjusted.

On the operating unit 70, an angle knob 71, an air/water supply button 72, a suction button 73, and a treatment tool insertion opening 74 are arranged. The angle knob 71 controls the bending portion 62 so that the bending portion 62 can bend in a desired direction. The air/water supply button 72 performs air supply operation and water supply operation. The suction button 73 performs suction operation. The treatment tool insertion opening 74 serves as an inlet for a treatment tool that is guided into a body.

The treatment tool insertion opening 74 communicates with the forceps port through a treatment tool insertion channel (not illustrated) provided inside the insertion portion 60. A sheath of an ultrasound treatment tool (not illustrated) can be inserted into the treatment tool insertion opening 74. The puncture needle 69 inserted into the sheath is caused to project from the forceps port, whereby the puncture needle 69 can be arranged within an observation field of the ultrasound probe 500 so as to be capable of moving back and forth.

As illustrated in FIG. 13, an ultrasound transducer array 45 of the ultrasound probe 500 has, for example, a plurality of ultrasound transducers 46 formed in a rectangular shape in a plan view. The ultrasound transducer array 45 includes a convex transducer group configured in such a manner that long sides of the ultrasound transducers 46 are joined to one another and curved and arranged in an arc shape. Specifically, in the ultrasound transducer array 45, for example, 100 ultrasound transducers 46 each having a short side of 0.1 mm or less are arranged on a side surface of an arc having a radius of 5 mm in a 180-degree direction. Although the ultrasound transducer array 45 illustrated in FIG. 13 employs the convex type, it is also possible to employ, for example, a radial type to which a two-dimensional array is applied or a linear transducer group that is not curved.

At one end portion of the ultrasound transducer array 45 formed in an arc shape, an electrode terminal 41 provided at one end portion of each ultrasound transducer 46 is arrayed. These electrode terminals 41 are coupled to respective signal lines 48 that are center conductors branching off from a plurality of coaxial cables 47 via a flexible substrate (FPC substrate). On the other end portion of the ultrasound transducer array 45, an electrode terminal 42 provided at the other end portion of each ultrasound transducer 46 is arrayed. These electrode terminals 42 are coupled to respective ground lines 49 (shields) branching off from the coaxial cables 47 via a shield connection electrode 43.

Using the ultrasound endoscope system 20 configured as described above, the ultrasound probe 500 that transmits and receives ultrasound is provided at the distal end of the insertion portion 60, an ultrasound image of an organ or the like obtained when the insertion portion 60 is inserted into a body of a subject is displayed on a display unit of the monitor 50, and an in-vivo image captured by an endoscope observation function is displayed on the display unit, whereby observation and diagnosis or the like of an object to be diagnosed can be performed.

INDUSTRIAL APPLICABILITY

As mentioned above, a cable connection structure according to the present invention is useful for an ultrasound probe or an imaging device configured such that a plurality of coaxial cables is connected to a substrate or the like, and particularly suitable for a small-sized endoscope device.

A cable connection structure according to some embodiments, it is possible to reduce a thickness of a connection portion between a cable and a substrate, and to suppress disconnection or a short circuit owing to small deformation of the cable at the connection portion. Since a shield and a shield connection electrode are directly connected, noise can be reduced.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cable connection structure comprising:
a substrate; and
a coaxial cable connected to the substrate, the coaxial cable having: a center conductor made of a conductive material; an inner insulator that coats an outer periphery of the center conductor; a shield that coats an outer periphery of the inner insulator; and an outer insulator that coats an outer periphery of the shield, wherein
the substrate has a first substrate and a second substrate,
the first substrate has a first base material made of an insulator and a center conductor connection electrode to which the center conductor is connected such that the center conductor connection electrode is formed in the first base material so as to be flush with the first base material,
the second substrate has a second base material made of an insulator and a shield connection electrode to which the shield is connected such that the shield connection electrode is formed in the second base material so as to be flush with the second base material,
the first and second substrates are stacked such that the shield connection electrode and the center conductor connection electrode are bared from an end portion of the substrate toward a connection surface of the substrate,
an end portion of the coaxial cable is processed such that the center conductor, the inner insulator, and the shield are exposed in a stepwise fashion from a distal end portion of the coaxial cable, and
the processed end portion of the coaxial cable is arranged on a connection part of the substrate so that the shield and the center conductor are respectively connected to the shield connection electrode and the center conductor connection electrode bared from the end portion of the substrate toward the connection surface of the substrate.

2. The cable connection structure according to claim 1, wherein
an exposed part of the inner insulator of the coaxial cable is arranged above the second substrate such that the outer periphery of the inner insulator does not come into contact with the second base material.

3. An endoscope device comprising at least one of an ultrasound probe and an imaging device, the ultrasound probe being configured to obtain information by means of ultrasound, the imaging device being configured to obtain image information, wherein
at least one of the ultrasound probe and the imaging device has the cable connection structure according to claim 1.

4. A cable connection structure comprising:
a first substrate formed of an insulator, the first substrate having a first surface, the first surface having a first center conductor connection electrode;
a second substrate formed of an insulator, the second substrate having a second surface, the second surface having a second center conductor connection electrode;

a ground sandwiched between the first substrate and the second substrate such that the ground is exposed from the first surface to form a first shield connection electrode and the ground is exposed from the second surface to form a second shield connection electrode;

a first coaxial cable connected to the first surface of the first substrate, the first coaxial cable having a first center conductor made of a conductive material, a first inner insulator covering an outer periphery of the first center conductor, a first shield that covers an outer periphery of the inner insulator, and a first outer insulator that covers an outer periphery of the first shield, the first center conductor being electrically connected to the first center conductor connection electrode and the first shield being electrically connected to the first shield connection electrode; and a second coaxial cable connected to the second surface of the second substrate, the second coaxial cable having a second center conductor made of a conductive material, a second inner insulator covering an outer periphery of the second center conductor, a second shield that covers an outer periphery of the inner insulator, and a second outer insulator that covers an outer periphery of the second shield, the second center conductor being electrically connected to the second center conductor connection electrode and the second shield being electrically connected to the second shield connection electrode.

5. The cable connection structure according to claim 4, wherein the first and second shield connection electrodes are formed on an edge of the first and second substrates, respectively.

6. The cable connection structure according to claim 4, wherein at least one of the first and second shield connection electrodes are exposed through a cutout formed in the respective first and second substrates.

7. The cable connection structure according to claim 4, wherein:

the first center conductor connection electrode and the first shield connection electrode are formed along a first longitudinal axis, the second center conductor connection electrode and the second shield connection electrode are formed along a second longitudinal axis; and the first longitudinal axis and the second longitudinal axis are parallel and offset in a direction perpendicular to the first and second longitudinal axes.

8. The cable connection structure according to claim 4, wherein the first center conductor connection electrode is further from the edge of the first substrate than the second center conductor connection electrode is from the edge of the second substrate.

9. The cable connection structure according to claim 4, wherein a length in a width direction of each of the first and second shield connection electrodes extending to an end portion of a respective one of the first and second substrates is shorter than a length in a width direction of the first and second substrates.

10. The cable connection structure according to claim 4, wherein exposed portions of the ground forming the first and second shield connection electrodes expose only a part of the ground that is connected to a respective one of the first and second shields, and a part of the ground that is not connected to the first and second shields is coated with the first and second substrates, respectively.

11. The cable connection structure according to claim 4, wherein the first center conductor connection electrode and the second center conductor connection electrode are arranged such that center positions of the first and second center conductor connection electrodes do not overlap in a width direction of the first and second substrates.

12. An endoscope device comprising at least one of an ultrasound probe and an imaging device, the ultrasound probe being configured to obtain information by means of ultrasound, the imaging device being configured to obtain image information, wherein at least one of the ultrasound probe and the imaging device has the cable connection structure according to claim 4.

* * * * *